United States Patent
Zollinger

(10) Patent No.: US 8,347,909 B2
(45) Date of Patent: Jan. 8, 2013

(54) FLOAT VALVE SYSTEM FOR A RESPIRATORY HUMIDIFICATION SYSTEM

(75) Inventor: Christopher Jesse Zollinger, Chino Hills, CA (US)

(73) Assignee: CareFusion 2200, Inc., San Diego, CA (US)

( * ) Notice: Subject to any disclaimer, the term of this patent is extended or adjusted under 35 U.S.C. 154(b) by 624 days.

(21) Appl. No.: 12/616,414

(22) Filed: Nov. 11, 2009

(65) Prior Publication Data

US 2011/0108028 A1  May 12, 2011

(51) Int. Cl.
*F16K 31/18* (2006.01)
*A62B 9/02* (2006.01)

(52) U.S. Cl. .................... 137/423; 137/433; 128/205.24

(58) Field of Classification Search ............. 128/203.11, 128/201.28, 204.14, 205.24; 137/423, 429, 137/433; 417/507–508
See application file for complete search history.

(56) References Cited

U.S. PATENT DOCUMENTS

| | | | |
|---|---|---|---|
| 4,529,867 A | 7/1985 | Velnosky et al. | |
| 4,913,140 A | 4/1990 | Orec et al. | |
| 5,445,143 A | 8/1995 | Sims | |
| RE35,153 E | 2/1996 | Chiu | |
| 5,669,083 A | 9/1997 | Leombruni, Sr. | |
| 5,945,038 A | 8/1999 | Anderson | |
| 6,129,110 A | 10/2000 | Kolb | |
| 6,427,984 B1 | 8/2002 | Mulvaney et al. | |
| 6,450,196 B1 * | 9/2002 | Bartos et al. | 137/414 |
| 6,745,800 B1 * | 6/2004 | Sansom | 141/198 |
| 6,988,497 B2 | 1/2006 | Levine | |
| 7,047,999 B2 | 5/2006 | Payne | |
| 7,182,321 B2 | 2/2007 | Huang et al. | |
| 7,306,205 B2 | 12/2007 | Huddart et al. | |
| 2004/0020998 A1 | 2/2004 | Stueble | |
| 2007/0132117 A1 | 6/2007 | Pujol et al. | |
| 2007/0157928 A1 | 7/2007 | Pujol et al. | |
| 2007/0240767 A1 | 10/2007 | Rustad et al. | |
| 2008/0054500 A1 | 3/2008 | Bradley et al. | |

FOREIGN PATENT DOCUMENTS

| | | |
|---|---|---|
| EP | 0 422 305 A1 | 4/1991 |
| EP | 0 589 429 A1 | 3/1994 |
| EP | 0589429 A1 | 3/1994 |
| EP | 0 903 524 A2 | 3/1999 |
| EP | 1 306 599 A2 | 5/2003 |
| EP | 1 366 881 A2 | 12/2003 |
| WO | 2008017892 A1 | 2/2008 |

OTHER PUBLICATIONS

PCT Search Report mailed Dec. 30, 2010 (11 pages).

* cited by examiner

*Primary Examiner* — Justine Yu
*Assistant Examiner* — Rachel Young

(57) ABSTRACT

A float valve system for controlling an amount of liquid in a chamber is disclosed that includes a first valve seat and a second valve seat. Liquid enters the chamber in a first direction to the first valve seat and is transferred in a second direction to the second valve seat. First and second actuating members are provided to selectively open and close the first valve seat and the second valve seat, respectively. A first float is coupled to the first actuating member so as to close the first valve seat upon fluid in the chamber reaching a first predetermined level and a second float is coupled to the second actuating member so as to close the second valve seat upon fluid in the chamber reaching a second predetermined level that is different from the first predetermined level.

16 Claims, 4 Drawing Sheets

FLOAT VALVE SYSTEM FOR A RESPIRATORY HUMIDIFICATION SYSTEM

BACKGROUND

Respiratory humidification systems are used in providing respiratory therapy to a patient. In general terms, the system includes a ventilator, humidifier and patient circuit. The ventilator supplies gases to a humidification chamber coupled with the humidifier. Water within the humidification chamber is heated by the humidifier, which produces water vapor that humidifies gases within the chamber. From the chamber, humidified gases are then carried to the patient through the patient circuit. Humidification chambers can employ a fluid control mechanism to prevent liquid from directly passing to the patient, as this situation can be very harmful to the patient.

Current fluid control mechanism include one or more valves that are operated in response to a level of liquid in the chamber. Single valve chambers can be prone to defects in the event of failure of the valve. As a result, some chambers employ a dual valve mechanism having a primary valve and secondary valve that operates to stop fluid from entering the chamber in the event of failure of the primary valve. Each of the valves are arranged coaxially, thus requiring an inner valve to be positioned within an outer valve. This arrangement requires a large sealing area for the outer valve as well as a relatively large force to seal the outer valve. Due to the large sealing area and large force required to close the outer valve, failure of the valve can result.

SUMMARY

In one aspect of concepts presented herein, a float valve system for controlling an amount of liquid in a chamber is disclosed that includes a first valve seat and a second valve seat. The first valve seat is adapted to receive fluid from outside the chamber in a first direction. The second valve seat is spaced apart from the first valve seat in a second direction that is different from the first direction. First and second actuating members are provided to selectively open and close the first valve seat and the second valve seat, respectively. A first float is coupled to the first actuating member so as to close the first valve seat upon fluid in the chamber reaching a first predetermined level and a second float is coupled to the second actuating member so as to close the second valve seat upon fluid in the chamber reaching a second predetermined level that is different from the first predetermined level.

In another aspect, a chamber for use in a respiratory humidification system is described. The chamber includes a valve assembly having a first valve seat adapted to receive fluid from outside the chamber in a first direction through a valve assembly inlet. Furthermore, the valve assembly includes a second valve seat spaced apart from the first valve seat in a second direction that is different from the first direction. The second valve seat is fluidly coupled to the first valve seat and adapted to transfer fluid to the chamber. A first actuating member is adapted to selectively open and close the first valve seat and a second actuating member is spaced apart from the first actuating member in the second direction. The second actuating member is adapted to selectively open and close the second valve seat. A first float is coupled to the first actuating member so as to close the first valve seat upon fluid in the chamber reaching a first predetermined level and a second float is coupled to the second actuating member so as to close the second valve seat upon fluid in the chamber reaching a second predetermined level that is different than the first predetermined level.

In another aspect, a method of controlling a level of liquid in a chamber is disclosed. The method includes providing a valve assembly in the chamber to receive liquid from outside the chamber. The valve assembly includes a support structure, a retaining element having a first valve seat and a second valve seat positioned therein, and a diaphragm positioned between the support structure and the retaining element. A first float and a second float are coupled to the support structure and fluid is transferred to the first valve seat in a first direction. Fluid is then transferred through a fluid conduit in a second direction different from the first direction. The diaphragm is urged against the first valve seat using the first float upon liquid in the chamber reaching a first predetermined level and the diaphragm is urged against the second valve seat using the second float upon liquid in the chamber reaching a second predetermined level that is different than the first predetermined level.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims. It is to be understood that the features of the various exemplary embodiments described herein may be combined with each other, unless specifically noted otherwise.

Figure 1:
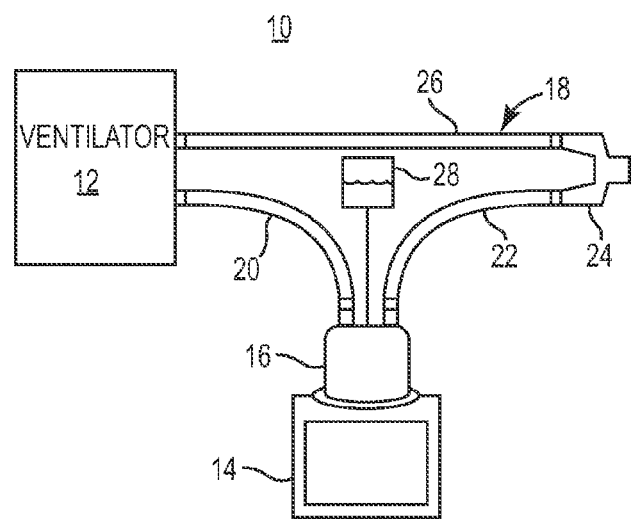
FIG. 1 is a schematic diagram of a respiratory humidification system.

FIG. 1 is a schematic view of a respiratory humidification system 10 including a ventilator 12, humidifier 14 having a humidification chamber 16 and a patient circuit 18. It is worth noting that system 10 is one exemplary environment for concepts presents herein. In other embodiments, system 10 can include additional components or have one or more components removed. For example, one other exemplary environment is a continuous positive airway pressure (CPAP) system. Ventilator 12 supplies gases to humidification chamber 16 through an initial conduit 20. Humidifier 14 heats and vaporizes water within the chamber 16. The vaporized water humidifies gas from ventilator 12, which is then output to patient circuit 18. Patient circuit 18 includes an inspiratory conduit (or limb) 22, a y-connector 24 and an expiratory conduit (or limb) 26. In other embodiments, for example a CPAP system, y-connector 24 and limb 26 can be eliminated.

Figure 2:
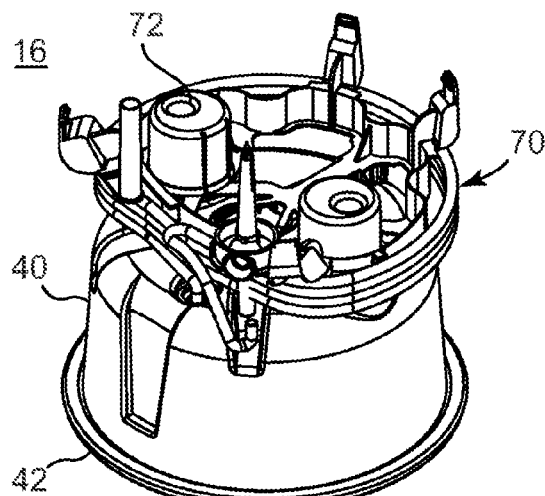
FIG. 2 is an isometric view of a humidification chamber.
Figure 3:
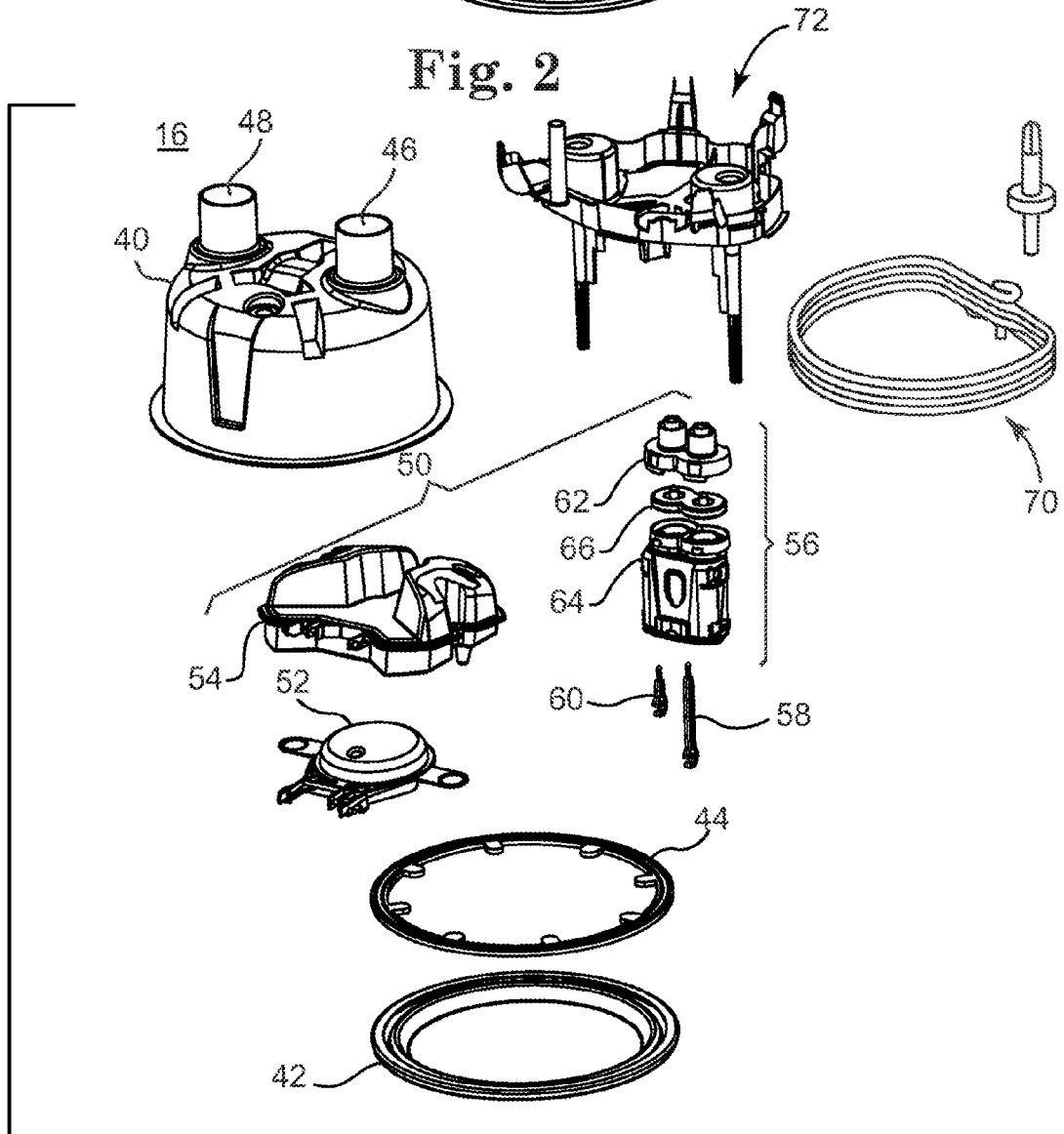
FIG. 3 is an exploded view of the humidification chamber of FIG. 2.
Figure 4:
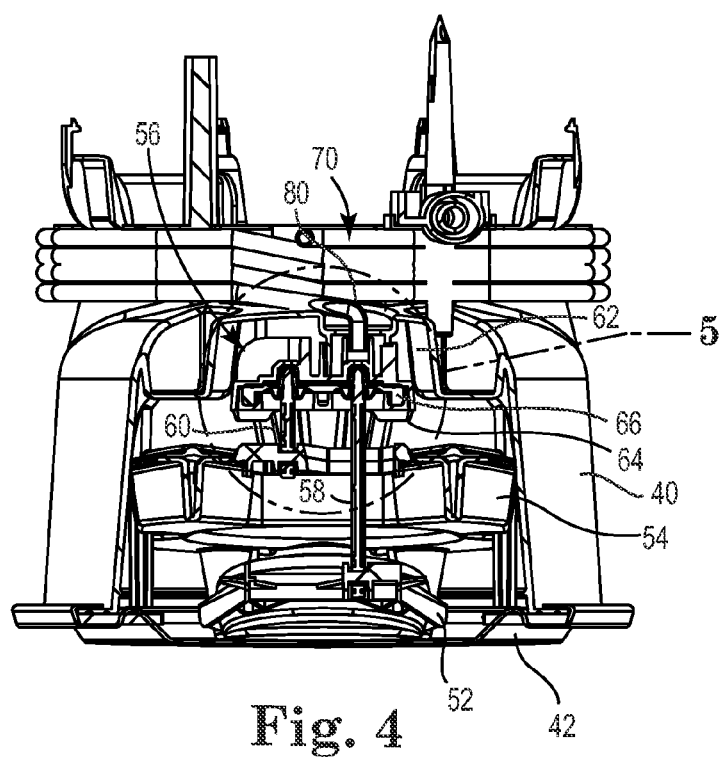
FIG. 4 is a sectional view of the humidification chamber of FIG. 2.

Inspiratory conduit 22 transmits humidified gases from chamber 16 to a patient through a y-connector 24. The y-connector 24 can be selectively coupled to a patient interface such as an endotracheal tube. Other patient interfaces can also be used, for example masks, nasal prongs, etc. After breathing in the humidified gases transferred from chamber 16, the patient can exhale, transmitting exhaled gases through expiratory conduit 26 back to ventilator 12. In one embodiment, inspiratory conduit 22 and expiratory conduit 26 can be heated with a helical wire as described in copending U.S. application Ser. No._____, entitled "Heated Conduit for Respiratory Humidification", filed on even date herewith, the contents of which are hereby incorporated by reference in their entirety. Liquid can be supplied to the chamber 16 from a fluid source 28, which, in one embodiment comprises a bag of liquid (e.g., water) fluidly coupled to the chamber 16. As discussed below, chamber 16 includes a float valve system to control the amount of liquid flowing from source 28 into chamber 16, and, in particular, the amount of liquid in chamber 16. With further reference to FIGS. 2-4, humidification chamber 16 includes a housing 40 coupled to a base plate 42. Positioned between housing 40 and base plate 42 is a gasket 44, which is configured to provide a water tight seal between housing 40 and base plate 42. Housing 40 further includes a gas inlet 46 adapted for coupling to conduit 20 and a gas outlet 48 for coupling to conduit 22 and transmitting humidified gas to conduit 22. During operation, gas flows into chamber 16 from ventilator 12 through gas inlet 46. Humidifier 14 (FIG. 1) provides heat to base plate 42, which evaporates liquid in chamber 16. From there, the gas within chamber 16 is humidified and transmitted to patient circuit 18 through gas outlet 48.

A float valve system 50 is positioned within housing 40 to control an amount of fluid within the chamber 16. In particular, float valve system 50 includes a lower float 52, an upper float 54 and a valve assembly 56. Lower float 52 is coupled to valve assembly 56 through a first actuating member 58 whereas upper float 54 is coupled to valve assembly 56 through a second actuating member 60. First actuating member 58 and second actuating member 60 are spaced apart from one another in a horizontal direction. Lower float 52 cooperates with valve assembly 56 to prevent fluid from entering chamber 16 when a level of liquid in the chamber 16 reaches a first predetermined level. In turn, upper float 54 cooperates with valve assembly 56 to prevent fluid from entering chamber 16 when a level of liquid in the chamber 16 reaches a second predetermined level. In this manner, lower float 52 and upper float 54 operate independently to selectively seal portions of valve assembly 56 such that further fluid is prevented from entering chamber 16. In one embodiment, the second predetermined level is greater than the first predetermined level. In a further embodiment, the first predetermined level is greater than the second predetermined level.

Valve assembly 56 includes a retaining element 62, a support structure 64 and a diaphragm 66 positioned between the retaining element 62 and the support structure 64. Both lower float 52 and upper float 54 are pivotally coupled to support structure 64. Diaphragm 66 is formed of a flexible material (e.g., silicone) configured to seal against retaining element 62. As liquid within the housing 40 rises, lower float 52 urges actuating member 58 against diaphragm 66 and towards retaining element 62. Likewise, upper float 54 urges actuating member 60 against diaphragm 66 toward retaining element 62. As discussed in greater detail below, liquid enters housing 40 through tubing 70, which is fluidly coupled to retaining element 62. From retaining element 62, liquid flows into chamber 16 until lower float 52 or upper float 54 operates to prevent liquid from entering chamber 16.

If desired, a locking assembly 72 can be provided during shipment of the humidification chamber 16 so as to retain the tubing 70 as well as lower float 52 and upper float 54 against base plate 42. The locking assembly 72 can also protect debris and/or other contaminants from entering chamber 16 through gas inlet 46 and/or gas outlet 48. The locking assembly 72 is removed from chamber 16 and disposed prior to operation of the chamber 16.

Figure 5:
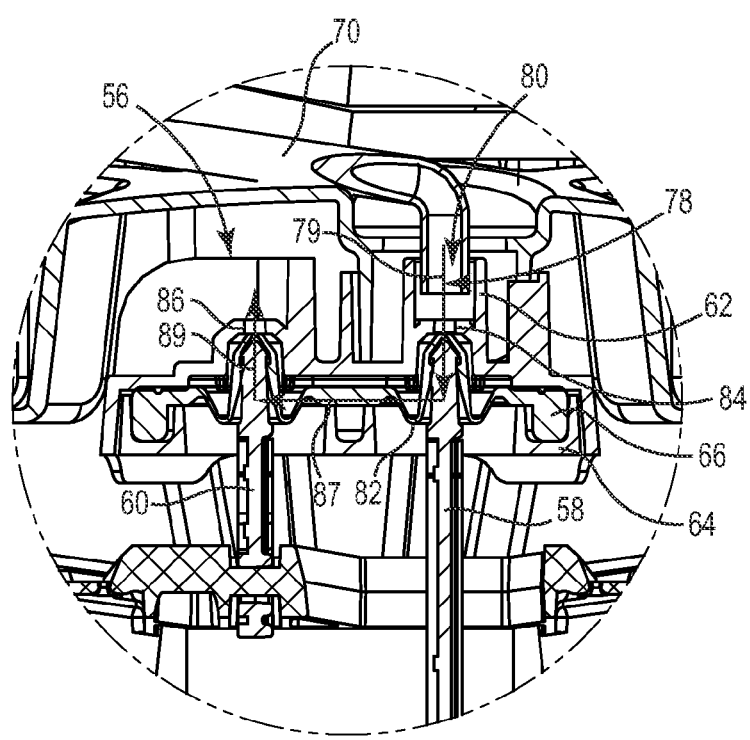
FIG. 5 is an enlarged view of a valve assembly illustrated in FIG. 4.

As discussed with reference to FIG. 5, a multi-directional fluid path 78 is established within valve assembly 56 upon entry of fluid into chamber 16. Path 78 includes a first vertical segment 79, wherein water enters housing 40 through a water inlet 80 coupled to tubing 70. Inlet 80 is fluidly coupled to retaining element 62, which transfers water to a valve conduit 82 between a lower portion of retaining element 62 and an upper portion of diaphragm 66. A valve seat 84 is positioned between retaining element 62 and valve conduit 82. Upon lower float 52 rising with a level of liquid in chamber 16, actuating rod 58 is configured to urge diaphragm 66 against valve seat 84, preventing further water from entering chamber 16. Lower float 52 can be positioned so as to seal valve seat 84 upon fluid in chamber 16 reaching a first predetermined level. If valve seat 84 remains open, fluid then passes through valve conduit 82 to a second valve seat 86 through a second, horizontal segment 87 of path 78. Second segment 87 transfers fluid in a direction that is different (e.g., perpendicular) than the direction of first segment 79. Upon upper float 54 rising with a level of liquid in chamber 16, actuating rod 60 is configured to urge diaphragm 66 against valve seat 86 to prevent further liquid from flowing into chamber 16. Path 78 further includes a third, vertical segment 89, transferring fluid from conduit 82 through valve seat 86. Third segment 89 is in a substantially opposite direction from first segment 79. In one embodiment, valve seat 84 and valve seat 86 are substantially the same size. After passing through valve seat 86, liquid ultimately enters chamber 16.

Upon entering chamber 16, the level of liquid will rise, causing float 52 to rise with the level. Actuating rod 58, being coupled to float 52, will urge diaphragm 66 against valve seat 84, thus preventing liquid from entering chamber 16 through inlet 80. In the event that a seal between diaphragm 66 and valve seat 84 fails, liquid will continue to enter chamber 16 until upper float 54 rises to urge diaphragm 66 against valve seat 86. In any event, fluid path 78 is substantially "U" shaped, transferring fluid entering inlet 80 to chamber 16 so as to provide small sealing areas for valve seats 84 and 86, thereby reducing the risk of leaks occurring in valve assembly 56.

In all, float valve system 50, through use of both lower float 52 and upper float 54, provides a redundant safety mechanism to prevent a fluid level within chamber 16 from rising too high. Thus, if one component in float valve system 50 fails, another component can be utilized to prevent further fluid from entering the chamber 16. For example, if one of the floats 52, 54 fail, the other float will operate to prevent fluid from entering the chamber.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A float valve system controlling an amount of liquid in a chamber, comprising:
    a first valve seat adapted to receive fluid from outside the chamber in a first direction through a chamber inlet;
    a second valve seat spaced apart from the first valve seat in a second direction, the second valve seat fluidly coupled to the first valve seat and adapted to receive fluid from the first valve seat;
    a first actuating member adapted to selectively open and close the first valve seat;
    a second actuating member spaced apart from the first actuating member in the second direction, the second actuating member adapted to selectively open and close the second valve seat;
    a first float coupled to the first actuating member so as to close the first valve seat upon fluid in the chamber reaching a first predetermined level; and
    a second float coupled to the second actuating member so as to close the second valve seat upon fluid in the chamber reaching a second predetermined level;
    a fluid conduit extending between the first valve seat and the second valve seat and adapted to transfer fluid from the first valve seat to the second valve seat in the second direction;
    wherein the fluid conduit is formed of a flexible diaphragm extending between the first valve seat and the second valve seat, the diaphragm adapted to deflect upon actuation of the first actuating member and the second actuating member.

2. The system of claim 1, wherein the chamber inlet is at a top of the chamber and the first direction is substantially vertical.

3. The system of claim 2 wherein the second direction is substantially perpendicular to the first direction.

4. The system of claim 1, wherein the first valve seat and second valve seat are substantially the same size.

5. The system of claim 1 wherein the first actuating member and the second actuating member operate independently.

6. The system of claim 1, further comprising an outlet transferring fluid from the second valve seat to the chamber in a third direction that is substantially opposite the first direction.

7. A chamber for use in a respiratory humidification system, comprising:
    a valve assembly, comprising:
        a first valve seat adapted to receive fluid from outside the chamber in a first direction through a valve assembly inlet;
        a second valve seat spaced apart from the first valve seat in a second direction, the second valve seat fluidly coupled to the first valve seat and adapted to transfer fluid to the chamber;
        a first actuating member adapted to selectively open and close the first valve seat;
        a second actuating member spaced apart from the first actuating member in the second direction, the second actuating member adapted to selectively open and close the second valve seat;
        a first float coupled to the first actuating member so as to close the first valve seat upon fluid in the chamber reaching a first predetermined level; and
        a second float coupled to the second actuating member so as to close the second valve seat upon fluid in the chamber reaching a second predetermined level;
        a fluid conduit extending between the first valve seat and the second valve seat and adapted to transfer fluid from the first valve seat to the second valve seat in the second direction;
        wherein the fluid conduit is formed of a flexible diaphragm extending between the first valve seat and the second valve seat, the diaphragm adapted to deflect upon actuation of the first actuating member and the second actuating member.

8. The chamber of claim 7, wherein the first direction is substantially vertical.

9. The chamber of claim 8 wherein the second direction is substantially perpendicular to the first direction.

10. The chamber of claim 7, wherein the first valve seat and second valve seat are substantially the same size.

11. The chamber of claim 7 wherein the first actuating member and the second actuating member operate independently.

12. The chamber of claim 7, further comprising an outlet transferring fluid from the second valve seat to the chamber in a third direction that is substantially opposite the first direction.

13. A method of controlling a level of liquid in a chamber, comprising:
    providing a valve assembly in the chamber to receive liquid from outside the chamber, the valve assembly including a support structure, a retaining element having a first valve seat and a second valve seat positioned therein and a diaphragm positioned between the support structure and the retaining element;
    coupling a first float and a second float to the support structure;
    transferring fluid through the first valve seat in a first direction;
    transferring fluid through a fluid conduit in a second direction;
    urging the diaphragm against the first valve seat using the first float upon liquid in the chamber reaching a first predetermined level; and
    urging the diaphragm against the second valve seat using the second float upon liquid in the chamber reaching a second predetermined level.

14. The method of claim 13, further comprising:
    transferring fluid through the second valve seat in a third direction different than the first direction and the second direction.

15. The method of claim 14 wherein the first direction and second direction are substantially vertical and the second direction is substantially horizontal.

16. The method of claim 13, further comprising:
    coupling a first actuating member between the first float and the support structure, the first actuating member configured to urge the diaphragm against the first valve seat; and
    coupling a second actuating member between the second float and the support structure, the second actuating member configured to urge the diaphragm against the second valve seat.

* * * * *